United States Patent
Salter et al.

(10) Patent No.: US 11,793,902 B2
(45) Date of Patent: Oct. 24, 2023

(54) SANITIZING SYSTEMS AND METHODS AND CONTROL STRATEGIES BASED ON WAVELENGTH

(71) Applicant: Ford Global Technologies, LLC, Dearborn, MI (US)

(72) Inventors: Stuart C. Salter, White Lake, MI (US); John Robert Van Wiemeersch, Novi, MI (US); Michael Hrecznyj, Livonia, MI (US); Paul Kenneth Dellock, Northville, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 376 days.

(21) Appl. No.: 16/822,538

(22) Filed: Mar. 18, 2020

(65) Prior Publication Data

US 2021/0290809 A1    Sep. 23, 2021

(51) Int. Cl.
*A61L 2/28*     (2006.01)
*A61L 2/24*     (2006.01)
*B60S 1/64*     (2006.01)
*A61L 2/10*     (2006.01)

(52) U.S. Cl.
CPC ........ *A61L 2/28* (2013.01); *A61L 2/10* (2013.01); *A61L 2/24* (2013.01); *B60S 1/64* (2013.01); *A61L 2202/11* (2013.01); *A61L 2202/14* (2013.01)

(58) Field of Classification Search
CPC ..... A61L 2/28; A61L 2/10; A61L 2/24; A61L 2202/11; A61L 2202/14; A61L 2202/17; A61L 2/26; B60S 1/64
See application file for complete search history.

(56) References Cited

U.S. PATENT DOCUMENTS

| 8,964,405 B2 | 2/2015 | La Porte et al. |
| 2003/0127506 A1* | 7/2003 | Braun, Jr. ............... A61L 2/202 232/31 |
| 2013/0004367 A1 | 1/2013 | Roberts |

(Continued)

FOREIGN PATENT DOCUMENTS

WO    2001/60419 A1    8/2001

OTHER PUBLICATIONS

"PhoneSoap Go 2-Pack," Web page <https://www.phonesoap.com/products/phonesoap-go-w-pack.html>, 9 pages, retrieved from the Internet on Dec. 21, 2020.

*Primary Examiner* — Regina M Yoo
(74) *Attorney, Agent, or Firm* — Frank Lollo; Eversheds Sutherland (US) LLP (57) ABSTRACT

Sanitizing devices and control strategies based on wavelength are provided herein. An example device includes an enclosure for receiving an object, a first cleaning element that emits radiation at a first wavelength adapted to sanitize or sterilize contaminants on the object, a contaminant exposing element that emits radiation at a second wavelength that illuminates the contaminants on the object, a notification element that emits visible light within the enclosure, the visible light having a selected hue, and a controller for executing a cleaning cycle that includes illuminating contaminants present on the object using the contaminant exposing element prior to sanitizing or sterilizing the contaminants present on the object using the first cleaning element.

11 Claims, 4 Drawing Sheets

(56) References Cited

U.S. PATENT DOCUMENTS

| | | | |
|---|---|---|---|
| 2015/0137747 A1* | 5/2015 | Salter | A61L 2/10 |
| | | | 320/108 |
| 2020/0061223 A1* | 2/2020 | Hallack | B60N 2/002 |
| 2021/0060191 A1* | 3/2021 | Dunham | A61L 2/10 |
| 2021/0278061 A1* | 9/2021 | Ben-Shmuel | F21V 33/0064 |

* cited by examiner

SANITIZING SYSTEMS AND METHODS AND CONTROL STRATEGIES BASED ON WAVELENGTH

FIELD

The present disclosure is generally directed to systems and methods for illuminating and sanitizing contaminants on objects through use of various wavelengths of light radiation, as well as control cycle strategies.

BACKGROUND

Certain wavelengths of ultraviolet (UV) spectrum electromagnetic radiation can be used as a germicide to sanitize and/or sterilize contaminated objects. Some devices use broad wavelength fluorescent tubes, but these devices contain heavy metals, which are environmentally unsafe. Due to regulatory compliance issues, broad wavelength fluorescent tubes are typically not used in a vehicle.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

The present disclosure pertains to sanitizing/sterilizing devices and associated control strategies. An example sanitizing/sterilizing device of the present disclosure can include a plurality of light emitting diode (LED) elements that collectively provide a broad spectrum of various wavelengths of electromagnetic radiation selected from any portion of the light spectrum. Individual LED elements can be configured to emit any of UV-A, UV-B, UV-C, IR, and visible light having a selected hue. Various LED elements can be used in combination to provide contaminant illumination and sanitization/sterilization of contaminants on a target object, such as a cellphone or the like.

In general, a cleaning element of an example device of the present disclosure can be tuned to sanitize or sterilize contaminants through wavelength modulation. For purposes of brevity and clarity of description, some descriptions may refer to sanitization or sterilization, or even generally to cleaning, but it will be understood that an element configured to sanitize can also be configured to sterilize.

In some instances, the cleaning device may include an enclosure having a plurality of LED elements that each emits radiation in at least one wavelength range. The example cleaning device can also include a charging means that can include a wired or wireless charging element for charging a device being cleaned.

The example cleaning device can comprise a controller that is configured to execute a specifically configured cleaning cycle where the LED elements may be cycled on or off in various sequences to provide a unique user experience. Cleaning strategies disclosed herein instill confidence with customers relative to the effectiveness of sterilization for a wide variety of different target objects. For example, a user may want to sterilize a phone or other objects and devices (e.g., watch, pacifier, etc.) during the drive cycle. The systems and methods herein may have a sterilization target time of 20 minutes, but a target cleaning cycle completion time of, for example, approximately 60, 45, 30, 25, 20, 15, 10, 5, and 1 minutes (or any time therebetween) can also be made available to a user. The target cleaning cycle completion time may be any suitable time greater than or less than 20 minutes.

The cleaning device can be controlled to both illuminate contaminants present on a target object, such as a mobile device, as well as clean contaminants using sanitation and/or sterilization. Post-cleaning processes can be used to illuminate remaining contaminants that can be removed through physical removal. That is, while contaminants have been sanitized/sterilized, physical remnants of these contaminants may remain. The control strategy can include displaying a message to the user that contaminants that remain illuminated after completion of sterilized/sanitized of a cleaning cycle may be wiped off.

ILLUSTRATIVE EMBODIMENTS

Figure 1:
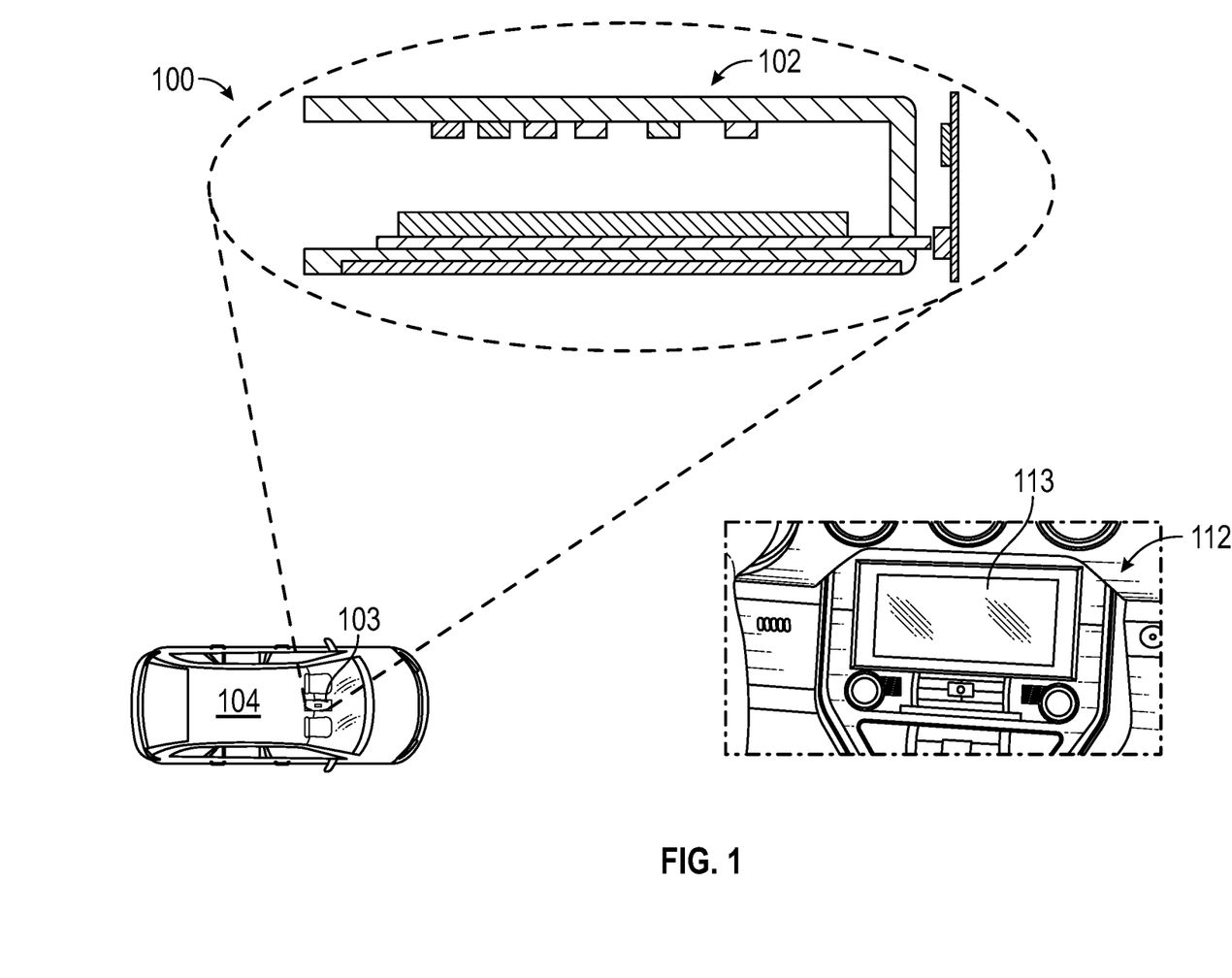
FIG. 1 depicts an illustrative architecture in which techniques and structures for providing the systems and methods disclosed herein may be implemented.

Turning now to the drawings, FIG. 1 depicts an illustrative architecture 100 in which techniques and structures of the present disclosure may be implemented. The architecture 100 can comprise a device 102 that can be positioned within a vehicle 104, such as a car. The device 102 can include a portable unit that can be used within the vehicle 104 and removed as desired. Alternatively, the device 102 can be integrated into an interior of the vehicle 104. For example, the device 102 can be integrated into a console 103 of the vehicle between driver and passenger front seats.

Figure 2:
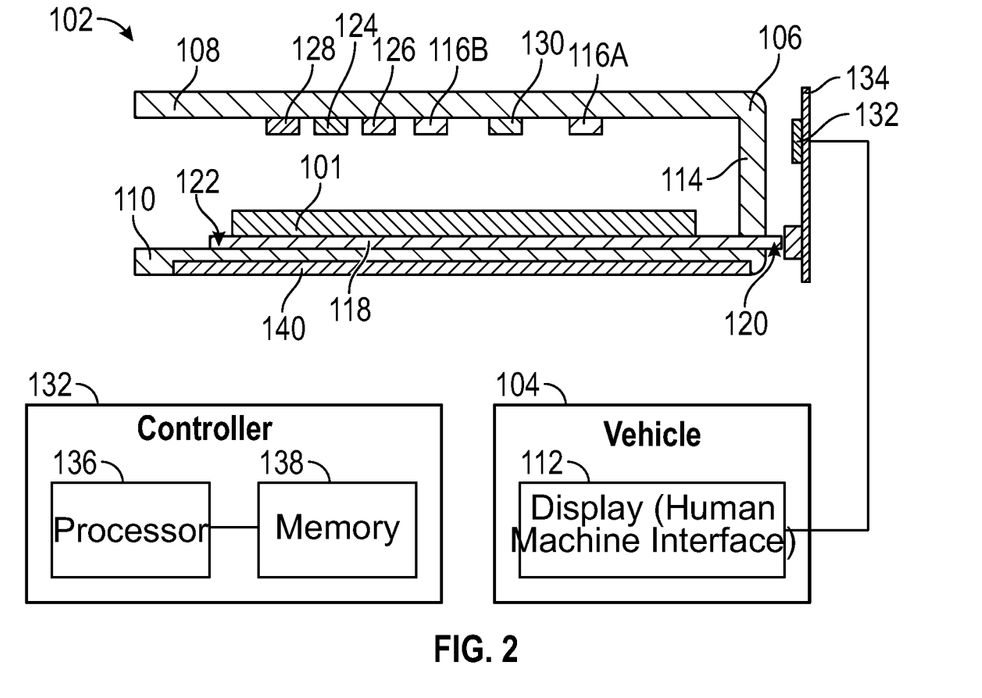
FIG. 2 is a cross-sectional view of an example sanitizer device constructed in accordance with the present disclosure.

In general, the device 102 can be configured to illuminate and clean a target object, such as a smartphone positioned inside the device 102. An example use case is illustrated in FIG. 2 and is described below. The device 102 can illuminate contaminants on the target object which allows a user to visibly identify contaminants. Illumination of contaminants can be accomplished by projecting UV-A and/or UV-B light onto the target object. Illumination can also be accomplished using infrared (IR) spectrum radiation, as well as visible light wavelength radiation. As will be discussed in greater detail, the device 102 can include one or more illuminating elements that are selected from any of UV-A light, UV-B light, IR light, visible light, or combinations thereof. It will be understood that UV-A and IR light may assist in accentuating visibility of organic matter in germs and other unsanitary organic matter which may exist on the target object.

The device 102 can be configured to use one or more of three bands of UV light to clean (e.g., sterilize or sanitize) devices: A, B, and/or C band radiation. An upper portion of the UV-A band contains visible light in the 380-400 nanometer wavelengths, but the exposure time to sterilize in the UV-A band would be in the order of days. The most efficient wavelength is approximately 264 nanometers in the UV-C band. This efficiency point enables sterilization in approximately ten minutes depending on the power level. To be sure, the device 102 can be configured to execute a cleaning cycle of having a user-specified duration.

In sum, the device 102 can be configured to use UV-C band light for optimum sterilization time(s). The device 102 may comprise an array of UV-C LEDs to accomplish adequate coverage of the target object. The UV-C LEDs can illuminate 360 degrees around the target object. As noted above, the device 102 can utilize various light elements to replicate other bands of light (UV-B, UV-A, visible, and IR) to allow users to visually see the state of the target object before cleaning and effectiveness during cleaning. The device 102 can be configured to manage activation time(s) of lighting elements as needed so as to minimize power draw (i.e., current consumption) during a cleaning cycle. The device 102 can be further configured to establish a customer human-machine-interface strategy to manage the fact some containments that (ex., tonic water, detergents, tooth paste, olive oil) present no bacteria or human fluid to the user but may still be visible after the cleaning cycle. The user can be instructed to wipe off these remaining contaminants through a display 112 within the vehicle 104. For example, the display 112 can include a message 113 that indicates that the phone has been sterilized and that any remaining contaminants can be wiped off.

Referring now to FIG. 2, which illustrates a cross-sectional view of the device 102. An example device can include at least one LED lighting element that emits light in the UV-A band, at least one LED lighting element that emits light in the UV-B band, at least one LED lighting element that emits light in the UV-C band and at least one LED lighting element that emits light in the IR band.

In more detail, the device 102 can comprise an enclosure 106 that has a first surface 108 and a second surface 110. The first surface 108 can be hingedly coupled to the second surface 110 to allow the target object 101 to be placed into the enclosure 106. Other coupling configurations between the first surface 108 and the second surface 110 can also be utilized. For example, the first surface 108 can include a retractable cover or a lid that covers the second surface 110. The first surface 108 can be coupled to the second surface 110 with a transition section 114 such that the enclosure 106 is substantially u-shaped.

The device 102 can comprise an array of cleaning elements such as cleaning element 116A and cleaning element 116B. These cleaning elements can also be referred to as first elements in some descriptions. For example, the cleaning element 116A can be referred to as a first element that emits ultraviolet radiation in the UV-C band. That is, the cleaning elements 116A and 116B each emit radiation at a first wavelength adapted to sanitize or sterilize contaminants. Multiple LED cleaning elements can be used due to the fact that LED lighting elements produce light in a focused manner and produce a spot lighting effect. For example, a UV-C band LED light may have only about a 15 nanometer diameter distribution pattern around its rated operation point of 265 nanometers.

In general, the array of cleaning elements 116A and 116B each emits ultraviolet radiation into the enclosure at a wavelength range of approximately 100 nanometers to approximately 280 nanometers, inclusive. In general, the array of cleaning elements 116A and 116B each emits UV radiation in the UV-C band of the electromagnetic radiation spectrum. Each of the cleaning elements 116A and 116B can comprise a LED lighting element that has been configured to emit UV-C band radiation. The array of cleaning elements can include fewer or more LED lighting elements than those illustrated and described. The number of the array of cleaning elements can be selected so as to achieve 360 degree coverage of a target object 101 in the enclosure 106. For example, the array of cleaning elements can be arranged on the second surface 110 of the enclosure 106.

A second cleaning element 118 in the form of a light pipe can be associated with the first surface 108 of the enclosure. The second cleaning element 118 can also emit a wavelength of radiation in the UV-C band. The array of cleaning elements and the second cleaning element 118 can be cooperatively activated to provide 360 degree cleaning of the target object 101. Rather than an optical guide, the second cleaning element 118 could include an array of cleaning elements as disclosed above.

The second cleaning element 118 can be assisted by a light pipe that tapers from a first end 120 to a second end 122 to deliver the UV light. In more detail, the second cleaning element 118 can be an optical silicone light pipe that tapers from two millimeters in diameter at the first end 120 to approximately one millimeter in diameter at the second end 122 to form a natural optic. Additionally, we will mold optics into the back to ensure even light intensity across the full length.

The device 102 can also comprise one or more contaminant exposing elements. These contaminant exposing elements can include LED lighting elements that have been configured to emit any of UV-A band radiation, UV-B band radiation, UV-C band radiation and/or IR radiation. These contaminant exposing elements emit radiation at a second wavelength that illuminates contaminants on the target object 101.

For example, a first contaminant exposing element 124 is a LED lighting element that emits ultraviolet radiation into the enclosure at a wavelength range of approximately 315 nanometers to approximately 400 nanometers, inclusive. The first contaminant exposing element 124 can alternatively operate at wavelengths of approximately 380 nanometers to 415 nanometers, inclusive. Broadly, the first contaminant exposing element 124 may emit UV-A band radiation.

Black lights may emit long-wave UV-A light with very little visible light which allows organic contaminants to be accentuated and fluorescent objects to glow without wash out from visible light. Also, low-power UV-A radiation emitted by black lights is not a hazard to skin or eyes and can be viewed without protection. It will be further understood that UV-A band light may also accentuate organic material that may contain germs, but it may also illuminate substances that are not sources of germs or infection and which may not be sterilized by UV-C light. The device 102 can be configured to prompt the user to physically clean the target object 101 to remove remaining contaminants that illuminate after being sanitized/sterilized. Some organic material that fluoresces under UV-A light include tonic water, antifreeze, vitamin A and B, laundry detergent, cosmetics, toothpaste, canola oil, and other known compounds. Blood and some other bodily fluids may also fluoresce under UV-A light. These may all remain on the target object after cleaning and can be removed through physical cleaning such as wiping the target object with a cloth.

A second contaminant exposing element 126 includes a LED lighting element that is configured to emit infrared radiation into the enclosure (e.g., wavelengths of radiation above 700 nanometers). The device 102 can comprise a third contaminant exposing element 128 that emits UV-B band radiation. For example, the third contaminant exposing element 128 emits ultraviolet radiation at a wavelength range of approximately 280 nanometers to approximately 315 nanometers, inclusive.

The device 102 can also comprise a notification element 130 that emits visible light within the enclosure. The notification element 130 can include a LED lighting element that emits visible light having a selected hue. For example, the notification element 130 can be configured to emit green light. The notification element 130 can be activated to identify to a user that a cleaning cycle is complete or nearly complete.

The various light emitting elements disclosed herein can be electrically coupled to a controller 132 through a printed circuit board 134. The controller 132 can be mounted directly to the printed circuit board 134. Individual LED elements can be coupled to the printed circuit board 134 using wires or traces.

The controller 132 can comprise a processor 136 and memory 138. The memory 138 stores instructions that are executed by the processor 136 to perform aspects of cleaning cycle management and notification, generally referred to as device control logic. When referring to operations executed by the controller 132 it will be understood that this includes the execution of instructions by the processor 136.

The device 102 can also comprise a charging element 140. The controller 132 can activate the charging element 140 to charge the target object 101. The charging element 140 can include an inductive charger coil that is over-molded (or otherwise integrated into) the first surface 108 using a thermally conductive plastic. The controller 132 is generally configured to perform a cleaning cycle that can comprise a coordinated set of procedures that include at least illumination of contaminants on the target object and contaminant sanitization/sterilization.

Figure 3:
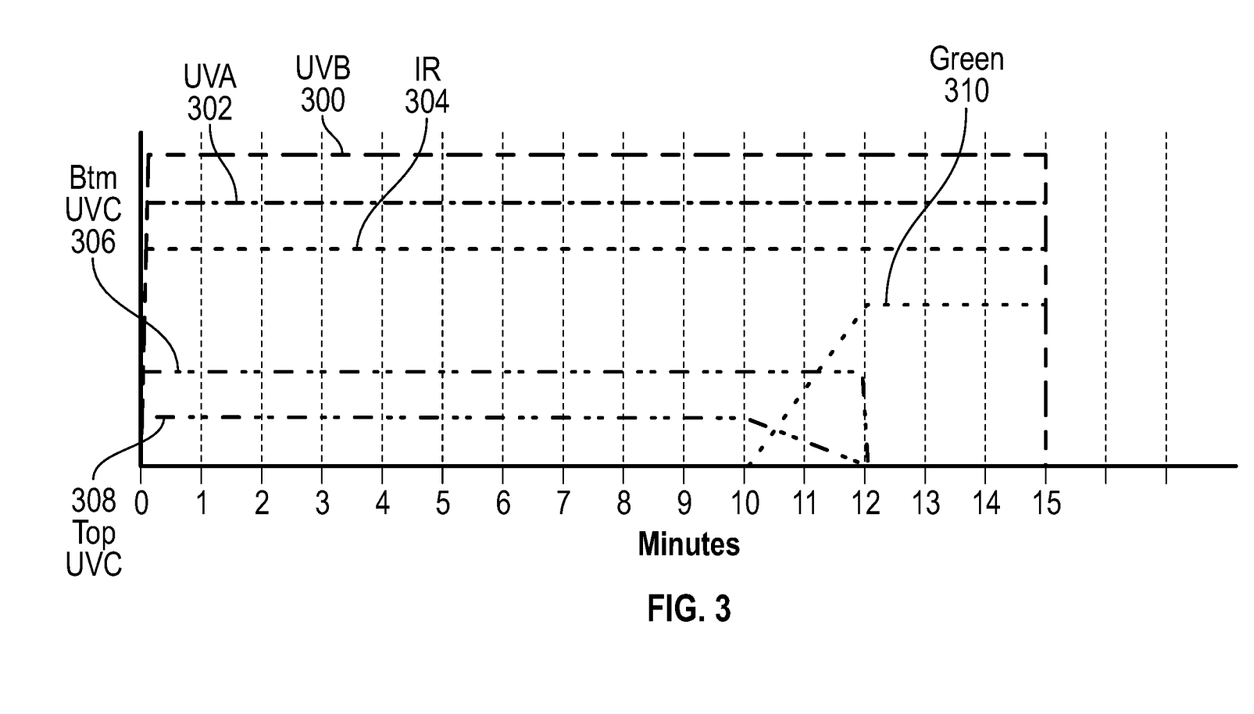
FIG. 3 graphically illustrates an example cleaning cycle control strategy of the present disclosure.

FIGS. 1 and 3 collectively illustrate an example cleaning cycle as performed by the controller 132. This example cleaning cycle is approximately 15 minutes in duration. The controller 132 can be configured to execute a cleaning cycle that includes activating any combination of the first contaminant exposing element 124, the second contaminant exposing element 126, and/or the third contaminant exposing element 128. These contaminant exposing elements can be operated for the duration of the cleaning cycle, from beginning to end at minute 15 as illustrated by lines 300 (UV-B), 302 (UV-A), and 304 (IR). While singular contaminant exposing elements in the UV-A, UV-B, and IR spectrums have been disclosed, it will be understood that more than one of each of these types of LED lighting elements can be included in the device 102.

The controller 132 can simultaneously activate the array of cleaning elements 116A and 116B and the second contaminant cleaning element 118 to sterilize/sanitize the target object. The cleaning cycle can include activating the array of cleaning elements 116A and 116B and the second contaminant cleaning element 118 for approximately ten to twelve minutes. In one use case, the second contaminant cleaning element 118 is operated at a continuous rate for 12 minutes as represented by line 306. The array of cleaning elements can be activated at a continuous rate for approximately ten minutes as illustrated by line 308. The controller 132 can then fade the radiation emitted by the array of cleaning elements 116A and 116B from minutes ten to twelve.

At approximately minute ten, the controller 132 can activate the notification element 130 to illuminate the enclosure with visible light of a particular hue, such as green. The controller 132 can be configured to incrementally power the notification element 130 from minute ten to minute twelve as illustrated by line 310. The notification element 130 is at full power from minute 12 to minute 15. The notification element 130 is incrementally activated as the cleaning elements are faded.

The controller 132 provides a visual cleaning "In-Progress" indication. That is, the cleaning elements 116A, 116B, and 118 can emit UV light having a wavelength of 264 nanometers that is invisible to the human eye. Thus, even though the device is "ON", it may appear to be unlit. Deep blue UV-A band light can be emitted to let the customer know the cleaning/sanitizing action is in progress.

General enclosure lighting at approximately 415 nanometers (visible light) and above 700 nanometers (IR) can cause body fluids (saliva, finger prints, and so forth) to fluoresce, providing a visual indication of cleanliness of the target object. The controller 132 can illuminate the enclosure with a glow or flash of green light when the cleaning cycle is finished. Because of the relative sensitivity of the human eye to maintain a similar appearance of intensity of lighting, more blue light UV-A elements may be incorporated into the enclosure than green elements.

In general, the controller 132 can be adapted to initially highlight evidence that cleaning is needed; that is to identify contaminants present on a target object through use of one or more types of contaminant exposing LED elements. If contaminants exist and if it is possible the contaminants can be illuminated, the controller 132 can perform a first level of LED activation. For example, illumination of contaminants using UV-A, UV-B, and/or IR radiation can be attempted at the first level.

If the contaminants cannot be illuminated at this first level, then the next level of illustration, which can be run in parallel, is to show visual light that follows the sequence of cleaning that is occurring as a result of the non-visible UV-C band light. The target object under the contaminant exposing LED elements is in need of sterilization and is being sterilized. The net effect is to increase customer confidence with respect to the perceived level of effectiveness of the cleaning process.

In one example use case, a device of the present disclosure can be configured to apply UV-C radiation throughout an entire sequence (e.g., cleaning cycle) with two or more UV-C LEDs associated with a top portion of an enclosure. UV-C LED elements can be supplemented with UV-B, UV-A, and IR LEDs that illuminate at a beginning of a cleaning cycle to visually illuminate contaminants. As the UV-C cleaning process nears completion time, the controller 132 can fade out the UV-C LED elements but maintain UV-B and IR LEDs in an active state.

For the bottom side of the enclosure, the controller 132 can activate the light pipe UV-C LED under the phone at full strength until the top side UV-C LED array is turned off. As the UV-C sanitization/sterilization process nears completion, the controller 132 can fade in a notification LED to signify completion and maintain the notification LED for a duration during which time the UV-A and/or IR LEDs can also remain illuminated.

The controller 132 can be configured to provide a user a screen message on the display 112 that if the target object still shows visual evidence of contaminants after the compartment is illuminated green (or another hue), these are chemicals (and not germs) that should be wiped off.

Figure 4:
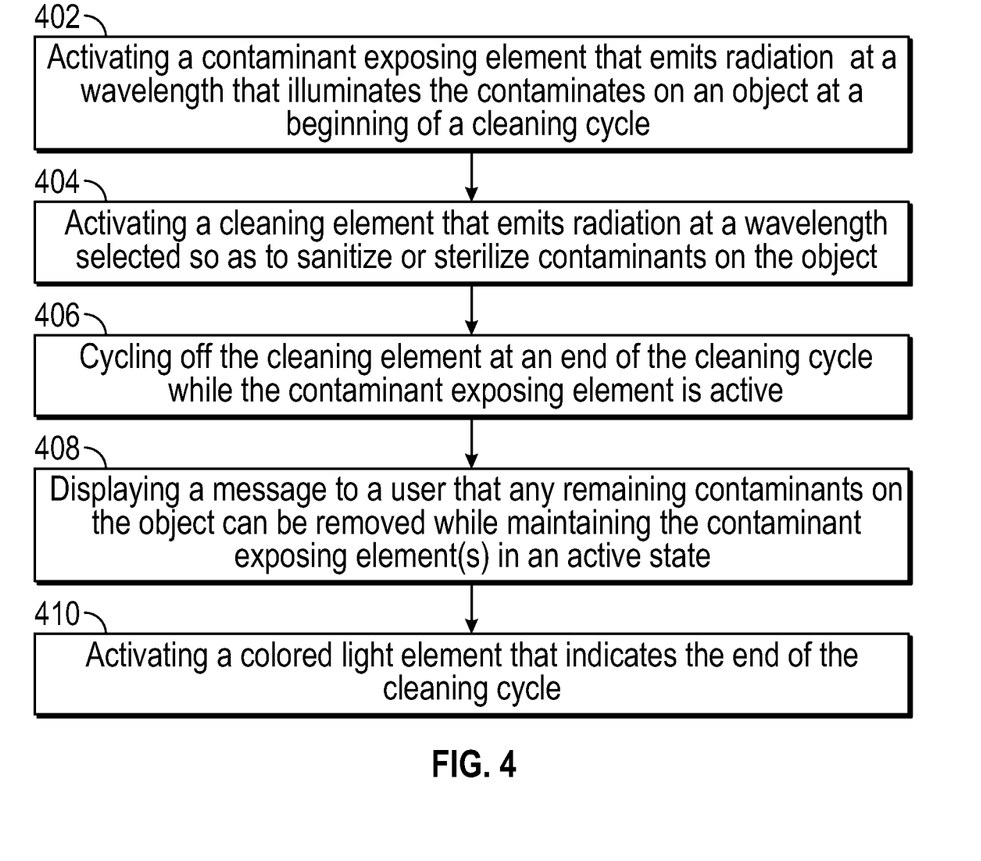
FIG. 4 is a flowchart of an example method of the present disclosure.

FIG. 4 illustrates an example method for controlling a cleaning cycle of a device of the present disclosure. The method can include a step 402 of activating a contaminant exposing element that emits radiation at a wavelength that illuminates the contaminants on an object at a beginning of a cleaning cycle. The wavelength of the contaminant exposing element includes ultraviolet-A or ultraviolet-B at approximately 380 nanometers to 415 nanometers, inclusive. As noted above, contaminant exposing elements can be used such as UV-A, UV-B, and/or IR.

The method can include a step 404 of activating a cleaning element that emits radiation at a wavelength selected so as to sanitize or sterilize contaminants on the object. The wavelength of the cleaning element corresponds to ultraviolet-C radiation. In some use cases, steps 402 and 404 can be executed in parallel.

The method can also include a step 406 of cycling off the cleaning element at an end of the cleaning cycle while the contaminant exposing element is active. The method can include a step 408 of displaying a message to a user that any remaining contaminants on the object can be removed while maintaining the contaminant exposing element(s) in an active state. The method can include a step 410 of activating a colored light element that indicates the end of the cleaning cycle. This colored light element can illuminate an interior of the enclosure. Alternatively, the colored light element could include an indicator positioned on an outside of the enclosure. The method can include a step of activating an inductive charging element to charge the object.

While the above disclosure has been described in specific scenarios involving vehicles, and specifically devices deployed in a console of a vehicle as an example, the present disclosure is not so limited. The example devices, systems, and/or methods can be advantageously deployed for use in any desired vehicle that can include cars (autonomous and non-autonomous), recreational vehicles (RVs), buses, trains, boats, planes, and the like. The example devices, systems, and/or methods can also be adapted for use in other locations such as homes, buildings, chairs, desks, schools, airports (and other transportation hubs), and so forth.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," and the like indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

Computer-executable instructions comprise, for example, instructions and data which, when executed at a processor, cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A device for a vehicle, the device comprising:
an enclosure for receiving an object, wherein the enclosure is generally u-shaped and comprises a first surface, a second surface, and a transition section that couples the first surface with the second surface;
a first cleaning element that emits radiation at a first wavelength adapted to sanitize or sterilize contaminants on the object;
a contaminant exposing element that emits radiation at a second wavelength that illuminates the contaminants on the object;
a notification element that emits visible light within the enclosure, the visible light having a selected hue; and
a controller comprising a processor and a memory for storing instructions, the processor executing the instructions to execute a cleaning cycle that includes illuminating contaminants present on the object using the contaminant exposing element prior to sanitizing or sterilizing the contaminants present on the object using the first cleaning element, wherein the cleaning cycle also comprises:
a first phase in which the first cleaning element and the contaminant exposing element are both activated;
a second phase, following the first phase, in which the first cleaning element is de-activated and the contaminant exposing element is maintained in an activated state; and
a third phase, following the second phase, in which the notification element is activated, wherein the third phase is at an end of the cleaning cycle.

2. The device according to claim 1, further comprising a second cleaning element comprising light pipe that tapers from a first end to a second end.

3. The device according to claim 2, wherein the light pipe being coupled to a printed circuit board, and wherein the controller is mounted to the printed circuit board.

4. The device according to claim 2, wherein the second cleaning element is mounted on the first surface of the enclosure that is opposite from the second surface of the enclosure onto which the first cleaning element is mounted, wherein the object is placed between the first cleaning element and the second cleaning element.

5. The device according to claim 1, further comprising an inductive charging element associated with the first surface of the enclosure.

6. A device, comprising:
an enclosure disposed within an interior of a vehicle and configured to receive an object, the enclosure comprising:
a first element that emits ultraviolet radiation into the enclosure at a wavelength range of approximately 100 nanometers to 280 nanometers, inclusive;
a second element that emits ultraviolet radiation into the enclosure at a wavelength range of approximately 315 nanometers to 400 nanometers, inclusive;
a third element that emits infrared radiation into the enclosure; and
a controller comprising a processor and a memory for storing instructions, the processor executing the instructions to execute a cleaning cycle that includes:
a first phase in which the first element and at least one of the second element and the third element is activated to expose and clean contaminants on the object;
a second phase, following the first phase, in which the first element is de-activated and the second element and/or the third element are maintained in an activated state; and
a third phase, following the second phase, in which a notification is provided indicating that at least a portion of the contaminants remain on the object, wherein the third phase is at an end of the cleaning cycle.

7. The device according to claim 6, further comprising a fourth element that emits ultraviolet radiation at a wavelength range of approximately 280 nanometers to 315 nanometers, inclusive.

8. The device according to claim 7, wherein the controller is configured to selectively fade the ultraviolet radiation emitted by the first element while the second element, the third element, and the fourth element remain on to identify remaining contaminants.

9. The device according to claim 6, further comprising a fifth element that emits visible light at a wavelength range of approximately 500 nanometers to 560 nanometers, inclusive, wherein the controller is configured to incrementally activate the fifth element while tapering off the first element.

10. The device according to claim 6, further comprising a sixth element that emits ultraviolet radiation at a wavelength range of approximately 100 nanometers to 280 nanometers, inclusive, wherein the sixth element is mounted on a first surface of the enclosure that is opposite from a second surface of the enclosure onto which the first element is mounted.

11. A vehicle comprising:
an enclosure disposed within an interior of the vehicle and configured to receive an object, the enclosure comprising:
a first element that emits ultraviolet radiation into the enclosure at a wavelength range of approximately 100 nanometers to 280 nanometers, inclusive;
a second element that emits ultraviolet radiation into the enclosure at a wavelength range of approximately 315 nanometers to 400 nanometers, inclusive;
a third element that emits infrared radiation into the enclosure; and
a controller comprising a processor and a memory for storing instructions, the processor executing the instructions to execute a cleaning cycle that includes:
a first phase in which the first element and at least one of the second element and the third element is activated to expose and clean contaminants on the object;
a second phase, following the first phase, in which the first element is de-activated and the second element and/or the third element are maintained in an activated state; and
a third phase, following the second phase, in which a notification is provided indicating that at least a portion of the contaminants remain on the object, wherein the third phase is at an end of the cleaning cycle.

* * * * *